United States Patent
Zhou et al.

(10) Patent No.: US 8,859,771 B2
(45) Date of Patent: Oct. 14, 2014

(54) ORGANIC ELECTROLUMINESCENT COMPOUND CONTAINING IRIDIUM, PREPARATION METHOD THEREOF AND ORGANIC ELECTROLUMINESCENT DEVICE

(75) Inventors: Mingjie Zhou, Shenzhen (CN); Ping Wang, Shenzhen (CN); Juanjuan Zhang, Shenzhen (CN); Zhenhua Zhang, Shenzhen (CN)

(73) Assignee: Ocean's King Lighting Science & Technology Co., Ltd., Shenzhen (CN)

( * ) Notice: Subject to any disclaimer, the term of this patent is extended or adjusted under 35 U.S.C. 154(b) by 0 days.

(21) Appl. No.: 14/130,183

(22) PCT Filed: Jun. 30, 2011

(86) PCT No.: PCT/CN2011/076723
§ 371 (c)(1),
(2), (4) Date: Jan. 30, 2014

(87) PCT Pub. No.: WO2013/000166
PCT Pub. Date: Jan. 3, 2013

(65) Prior Publication Data
US 2014/0142310 A1    May 22, 2014

(51) Int. Cl.
*C07F 15/00*    (2006.01)
*C07F 5/02*    (2006.01)

(52) U.S. Cl.
USPC ..................................... 546/4; 546/13; 546/5

(58) Field of Classification Search
USPC .......................... 546/4, 13; 313/504; 428/690
See application file for complete search history.

(56) References Cited

U.S. PATENT DOCUMENTS

2005/0170209 A1    8/2005  Lee et al.
2011/0049496 A1    3/2011  Fukuzaki

FOREIGN PATENT DOCUMENTS

JP    2007-161673 A    6/2007
WO    2011/024986 A1    3/2011

*Primary Examiner* — Charanjit Aulakh
(74) *Attorney, Agent, or Firm* — Fox Rothschild LLP

(57) ABSTRACT

An organic electroluminescent compound containing Iridium, preparation method thereof and an organic electroluminescent device are disclosed. The compound is represented by the structure (2), wherein, R is $C_1$~$C_4$ alkyl. The structure of the compound contains bipyridine ligand, also carries alkoxy group and fluorine atom, which improves its carrier injection and transfer ability, and increases its internal quantum efficiency and electroluminescent efficiency. Furthermore, the compound uses strong field ligand 2-pyridine carboxylic acid as assistant ligand, which causes an effective blue shift of its emission spectrum and increases light-emitting efficiency of blue light phosphorescence greatly.

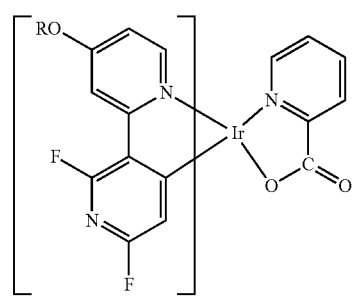

(2)

8 Claims, 1 Drawing Sheet

ORGANIC ELECTROLUMINESCENT COMPOUND CONTAINING IRIDIUM, PREPARATION METHOD THEREOF AND ORGANIC ELECTROLUMINESCENT DEVICE

CROSS REFERENCE TO RELATED APPLICATIONS

The present application is the U.S. National Phase of International Patent Application Serial No. PCT/CN11/76723, filed Jun. 30, 2011, the contents of which are hereby incorporated by reference in its entirety.

TECHNICAL FIELD

The present invention relates to the field of optoelectronic materials, in particular to an organic electroluminescent compound containing Iridium, preparation method thereof. The present invention further relates to an organic electroluminescent device using the organic electroluminescent compound containing Iridium as the light emitting layer.

BACKGROUND ART

Organic electroluminescent (EL) is a luminous phenomenon of an organic material under the effect of an electric field, of which the electrical energy is directly converted to light energy. In an early time, due to the high driving voltage and low luminous efficiency of the thus prepared device, study on organic electroluminescent devices was at a standstill. Until 1987, Tang et al from the United States Kodak as disclosed in the literature and U.S. Pat. No. 4,356,429 invented a dense and high-quality film by making use of 8-hydroxyquinoline aluminum ($Alq_3$) as the light-emitting material together with an aromatic diamine, and resulted in the formation of an organic electroluminescence device exhibiting high efficiency, low operating voltage, high brightness, and opened a new prologue on organic electroluminescent materials research. However, due to spin-statistical theory, the limit of the theoretical internal quantum efficiency of a fluorescent material is just 25%, since then the way of making full use of the remaining 75% of the phosphorescence to achieve higher efficiency has become a hot research direction in this field. In 1997, Forrest et al discovered the phenomenon of electrophosphorescence, the internal quantum efficiency of the organic electroluminescent material exceeded the 25% limit, which took the research on the organic electroluminescent materials into a new era.

In subsequent studies, the small molecule-doped transition metal complexes such as Iridium, ruthenium, and platinum complexes have become a research focus. The advantage of such complexes lies in achievement of high emission energy obtained from their triplet state. And among them, due to the good stability of the metallic Iridium (III) compounds which allows a mild reaction condition during synthesis, and to their high electroluminescent properties, these compounds has been occupied a dominant position in the subsequent study process. And in order to get a full color display device, generally red-, green- and blue-emitting materials having excellent performance must also be obtained. As compared with the red- and green-emitting materials, the development of blue-emitting material is lagging behind, the improvement of the efficiency and color purity of blue materials has become one of the breakthrough point. To date, Iridium(III)bis[2-(4, 6-difluorophenyl)pyridinato-N,$C^{2'}$](picolinato) (FIrpic) is one of the Ir(III) metal-organic complexes blue electrophosphorescence materials the most frequently reported in the patent literature. Although various optimization have been conducted on FIrpic based OLED structure, and the device performance has also been improved greatly, the biggest weakness of FIrpic is that it emits sky blue, the color purity of blue light is poor, making the CIE of the thus prepared OLED device varying in (0.13 to 0.17, 0.29 to 0.39). Therefore, the development of high-purity blue phosphorescent organic electroluminescent materials has become a major trend in expanding the research work on blue electrophosphorescence materials.

DISCLOSURE OF THE INVENTION

The object of the present invention is to provide an organic electroluminescent compound containing Iridium capable of emitting blue light phosphorescence.

The organic electroluminescent compound containing Iridium according to the present invention has the following structural formula:

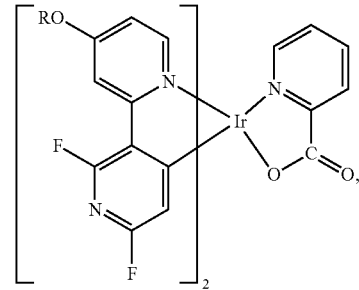

wherein R is $C_1$~$C_4$ alkyl.

Another object of the present invention is to provide a method of preparing the above-mentioned organic electroluminescent compound containing Iridium, which comprises the following steps:

S1: under an oxygen-free atmosphere, compound A of structural formula

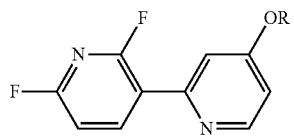

and Iridium trichloride trihydrate in a molar ratio of 3:1 to 5:1 are added to the first organic solvent (such as 2-ethoxyethanol), and dissolved to react in the formation of double-bridged compound B of structural formula

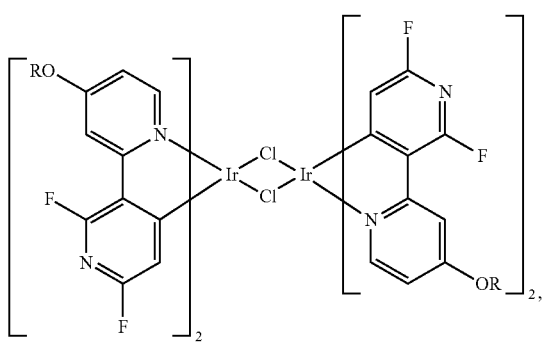

wherein, R is $C_1$~$C_4$ alkyl;

S2: under an oxygen-free atmosphere, the said double-bridged compound B and 2-picolinic acid in a molar ratio of 1:2.5 to 1:3.5 are added to the second organic solvent (such as 1,2-dichloroethane, glycerol, 2-ethoxyethanol or tetrahydrofuran) to undergo ligand exchange in the formation of said organic electroluminescent compound containing Iridium of structural formula

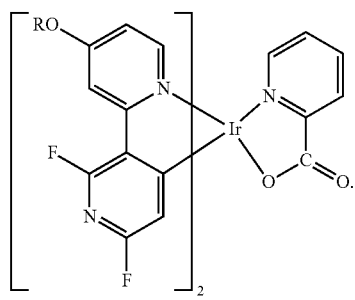

In step S1 of said method of preparing the above-mentioned organic electroluminescent compound containing Iridium, said compound A is prepared according to the following steps:

S11: under an oxygen-free and anhydrous atmosphere, compound D of structural formula

and lithium diisopropylamide in a molar ratio of 1.2:1 are added to a solution of tetrahydrofuran (THF) and undergo reaction at −78° C.; trimethyl borate is then added to the reaction mixture to undergo a reaction at room temperature in the formation of compound E of structural formula

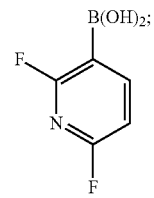 [SMILES: OB(O)c1ccc(F)nc1F]

S12: said compound E and compound F of structural formula

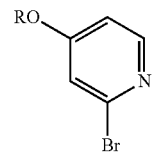

in a molar ratio of 1.5:1~2:1 are added to the third organic solvent (e.g. tetrahydrofuran, dioxane, toluene or dimethyl sulfoxide) containing a catalyst (e.g. a mixture of $K_2CO_3$ solution and $Pd(PPh_3)_4$, the molar amount of $K_2CO_3$ is 10-fold over the molar amount of compound F, the molar amount of Pd $(PPh_3)_4$ is 0.5% of the molar amount of compound F) to undergo Suzuki coupling reaction in the formation of said compound A; wherein in said compound F, R is $C_1$~$C_4$ alkyl.

Further, said step S11 comprises the step of purifying said compound E:

quenching the reaction in the reaction mixture with an addition of an aqueous solution of 5 wt % NaOH; followed by adjusting the pH of the reaction mixture to neutral using an aqueous solution of 3N HCl; and then extracting the mixture several times with ethyl acetate and combining the organic phases; finally concentrating the organic phrase to give the purified compound E.

Further, said step S12 comprises the step of purifying said compound A:

adding an appropriate amount of distilled water to the reaction mixture containing said compound A; then extracting several times with ethyl acetate, and combining the organic phases; drying the organic phase over anhydrous $MgSO_4$, followed by filtration and concentration of the filtrate; finally subjecting the filtrate residue to silica gel column chromatography using a mixture of ethyl acetate and n-hexane as eluent to obtain said purified compound A.

Still another object of the present invention is to provide an electroluminescent device, the light emitting layer of said electroluminescent device comprises an organic electroluminescent compound containing Iridium, said organic electroluminescent compound containing Iridium has the following structural formula:

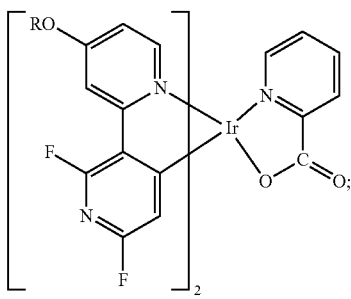

wherein R is $C_1$~$C_4$ alkyl.

The structure of the organic electroluminescent compound containing Iridium according to the present invention contains bipyridine ligand, and carries alkoxy group and fluorine atom, which improves its carrier injection and transfer ability, and increases its internal quantum efficiency and electroluminescent efficiency. Furthermore, the organic electroluminescent compound containing Iridium uses strong field ligand 2-picolinato as assistant ligand, which causes an effective blue shift of its emission spectrum and increases light-emitting efficiency of blue light phosphorescence greatly.

DETAILED DESCRIPTION OF THE EMBODIMENTS

Figure 1:
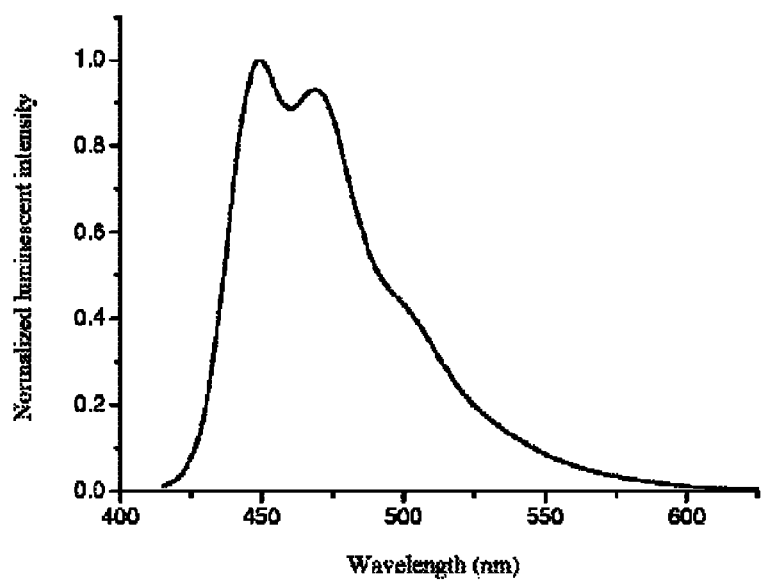
FIG. 1 shows the emission spectrum of the organic electroluminescent compound containing Iridium of Example 1.

The present invention provides an organic electroluminescent compound containing Iridium, which metal Iridium (Ir)-organic complex is a phosphorescent material having a relatively short phosphorescence lifetime (1~14 μs); said organic electroluminescent compound containing Iridium has the formula (dfpyORpy)$_2$Irpic; wherein, dfpy represents a pyridine ring of the cyclometalated ligand on which the 2 and 6-position of the pyridine ring are substituted by two fluorine atoms; ORpy represents another pyridine ring of the cyclometalated ligand on which the 4-position of the pyridine ring is alkoxy-substituted; the two pyridine rings are connected to each other in forming a bipyridine via 2- and 3-position, respectively; pic represents picolinato that acts as auxiliary ligand complex. Said organic electroluminescent compound containing Iridium has the following structural formula:

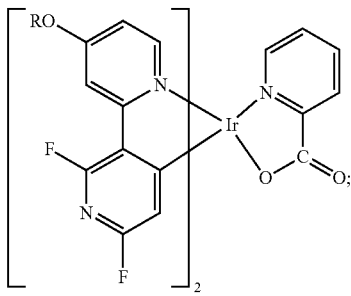

wherein, "2" means the structural formula contains two ligands of formula

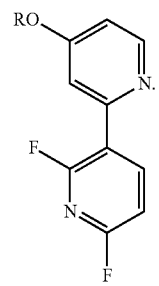

Expansion of the structural formula gives the structure as follows:

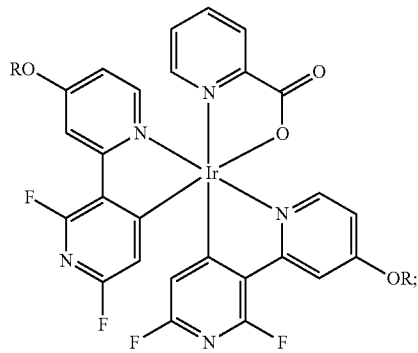

wherein, R is $C_1$~$C_4$ alkyl.

The structure of the organic electroluminescent compound containing Iridium according to the present invention contains bipyridine ligand, and carries alkoxy group and fluorine atom, which improves its carrier injection and transfer ability, and increases its internal quantum efficiency and electroluminescent efficiency. Furthermore, the organic electroluminescent compound containing Iridium uses strong field ligand 2-picolinato as assistant ligand, which causes an effective blue shift of its emission spectrum and increases light-emitting efficiency of blue light phosphorescence greatly.

The method of preparing said organic electroluminescent compound containing Iridium comprises the following steps:

S1: under an oxygen-free atmosphere (consisting of inert gas, e.g. nitrogen or argon atmosphere), compound A of structural formula

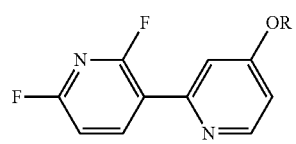

and Iridium trichloride trihydrate (IrCl$_3$.3H$_2$O) in a molar ratio of 3:1 to 5:1 (preferably 4:1) are added to the first organic solvent (such as 2-ethoxyethanol), and dissolved to react in the formation of a double-bridged compound B of structural formula

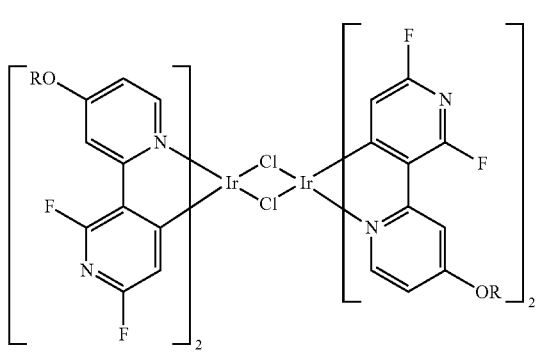

((dfpyORpy)₂Ir(μ-Cl)-(dfpyORpy)₂); wherein, R is C₁~C₄ alkyl; the reaction formula is as follows:

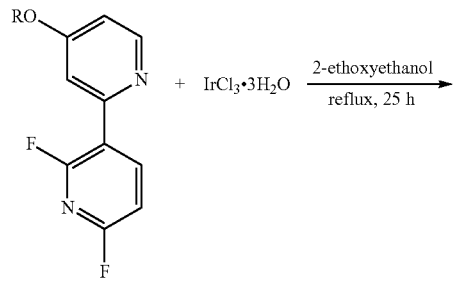

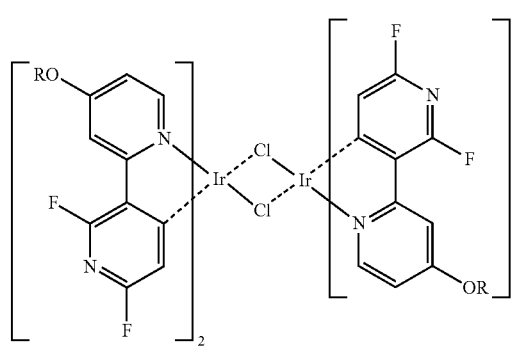

S2: under an oxygen-free atmosphere (consisting of inert gas, e.g. nitrogen or argon atmosphere), said double-bridged compound B and 2-picolinic acid in a molar ratio of 1:2.5 to 1:3.5 (preferably 1:3) are added to the second organic solvent (such as 1,2-dichloroethane, glycerol, 2-ethoxyethanol or tetrahydrofuran (THF)) to undergo ligand exchange in the presence of a co-catalyst consisting of sodium methoxide and silver trifluoroacetate under reflux condition to form said organic electroluminescent compound containing Iridium of structural formula

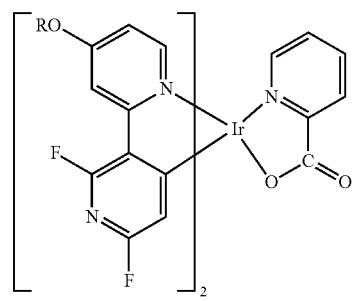

(i.e. (dfpyORpy)₂Irpic; the reaction formula is as follows:

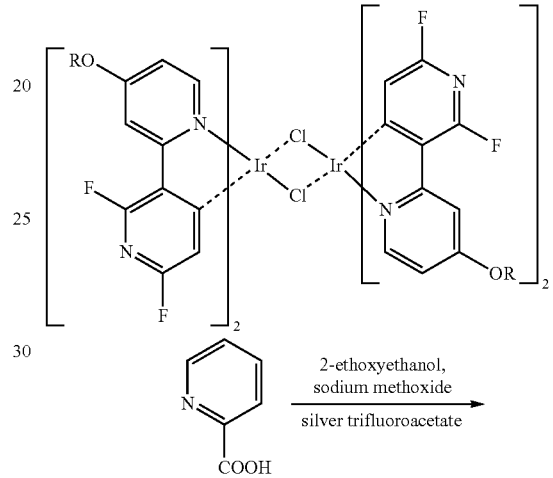

In step S1 of said method of preparing the above-mentioned organic electroluminescent compound containing Iridium, said compound A is prepared according to the following steps:

S11: under an oxygen-free and anhydrous atmosphere (consisting of inert gas, e.g. nitrogen or argon atmosphere), compound D of structural formula

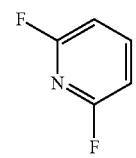

(i.e., 2,6-difluoropyridine) and lithium diisopropylamide (LDA) in a molar ratio of 1.2:1 are added to a solution of tetrahydrofuran (THF) and undergo reaction at −78° C. for 0.5 to 2 h to form 2,6-difluoropyridyl-3-lithium; 12.5 mmol of trimethyl borate (B(OMe)₃) is then added to the reaction mixture to allow a reaction between 2,6-difluoropyridyl-3-lithium and trimethyl borate (B(OMe)₃) at room temperature in the formation of compound E of structural formula

(i.e., 2,6-difluoro-pyridyl-3-boronic acid); the reaction formula is as follows:

S12: said compound E and compound F of structural formula

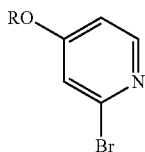

(i.e., 4-alkyl-2-bromopyridine) in a molar ratio of 1.5:1~2:1 (preferably 1.6:1) are added to the third organic solvent (e.g. tetrahydrofuran, dioxane, toluene or dimethyl sulfoxide) containing a catalyst (e.g. a mixture of K₂CO₃ solution and Pd(PPh₃)₄, the molar amount of K₂CO₃ is 10-fold over the molar amount of compound F, the molar amount of Pd (PPh₃)₄ is 0.5% of the molar amount of compound F) to undergo Suzuki coupling reaction in the formation of said compound A; wherein in said compound F, R is $C_1$~$C_4$ alkyl; the reaction formula is as follows:

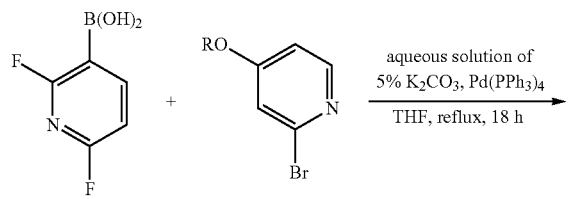

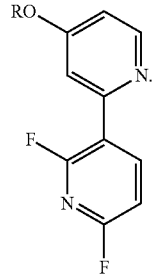

Further, said step S11 comprises the step of purifying said compound E:

quenching the reaction in the reaction mixture with an addition of an aqueous solution of 5 wt % NaOH; followed by adjusting the pH of the reaction mixture to neutral using an aqueous solution of 3N HCl; and then extracting the mixture several times with ethyl acetate and combining the organic phases; finally concentrating the organic phrase to give the purified compound E.

Further, said step S12 comprises the step of purifying said compound A:

adding an appropriate amount of distilled water to the reaction mixture containing said compound A; then extracting several times with ethyl acetate, and combining the organic phases; drying the organic phase over anhydrous MgSO₄, followed by filtration and concentration of the filtrate; finally subjecting the filtrate residue to silica gel column chromatography using a mixture of ethyl acetate and n-hexane as eluent to obtain said purified compound A.

In the above-mentioned method of preparing said organic electroluminescent compound containing Iridium, in order for obtaining compound B of higher purity, compound B prepared from step S1 are subjected to a purification process as follows:

S11: concentrating the reaction mixture under reduced pressure;

S12: subjecting the concentrated solution to silica gel column chromatography using dichloromethane as eluent to obtain said purified compound B.

Similarly, in the above-mentioned method of preparing said organic electroluminescent compound containing Iridium, in order for obtaining an organic electroluminescent compound containing Iridium of higher purity, said organic electroluminescent compound containing Iridium prepared from step S2 are subjected to a purification process as follows:

S21: properly concentrating the reaction mixture containing the organic electroluminescent compound containing Iridium, that is to remove part of the solvent, adding a suitable amount of distilled water for precipitating the solid.

S22: filtering the crude product, and subjecting to ultrasonic washing with sequential use of n-hexane, diethyl ether.

S23: subjecting the crude product to silica gel column chromatography using a mixture of n-hexane and dichloromethane as eluent to obtain said purified organic electroluminescent compound containing Iridium.

The organic electroluminescent compound containing Iridium and the main material in the light emitting layer of the organic electroluminescent device has good compatibility, which can be used in the light emitting layer as the doping guest widely used for the preparation of blue or white phosphorescent electroluminescent devices; said organic electroluminescent compound containing Iridium has the following structural formula:

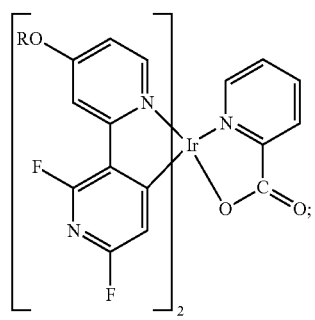

wherein, R is $C_1$~$C_4$ alkyl.

The structure of the organic electroluminescent compound containing Iridium according to the present invention contains bipyridine ligand, and carries alkoxy group and fluorine atom, which improves its carrier injection and transfer ability, and increases its internal quantum efficiency and electroluminescent efficiency. Furthermore, the organic electroluminescent compound containing Iridium uses strong field ligand 2-picolinato as assistant ligand, which causes an effective blue shift of its emission spectrum and increases light-emitting efficiency of blue light phosphorescence greatly.

Detailed description to the best embodiments of the present invention will now be given with reference to the drawings below:

Example 1

The organic electroluminescent compound containing Iridium of the embodiment according to the present invention, namely Iridium(III)bis(2',6'-difluoro-4-methoxy-2,3'-bipyridinato-N,C$^{2'}$) (2-picolinato) [(dfypmopy)$_2$Irpic], wherein R is methyl:

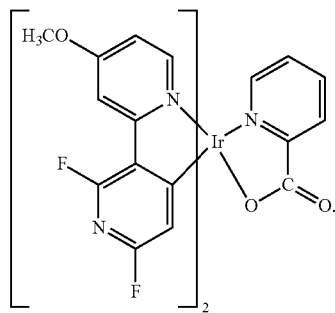

The method of preparing Iridium(III)bis(2',6'-difluoro-4-methoxy-2,3'-bipyridinato-N,C$^{2'}$) (2-picolinato) is as follows:

(1) Synthesis of 2,6-difluoro-pyridyl-3-boronic acid

Under a nitrogen atmosphere, 7.5 mL (12 mmol) of 1.6 M lithium diisopropylamine and 0.91 mL (10 mmol) of 2,6-difluoropyridine were added to 40 mL of tetrahydrofuran, and kept reacting at −78° C. for 1 h. After the addition of 1.40 mL (12.5 mmol) of trimethyl borate, the temperature was naturally warmed to room temperature and the mixture was kept mixing to react for 1 h. The reaction mixture was quenched by slowly adding 20 mL of an aqueous solution of 5 wt % NaOH, after stirring for 10 min, an aqueous solution of 3N HCl was added dropwisely to adjust the pH to neutral. The mixture was extracted several times with ethyl acetate and the organic phases were combined, solvent was removed by rotary evaporation to give 1.43 g of white solid in 90% yield.

$^1$H NMR (400 MHz, CDCl$_3$, ppm): δ 8.45 (d, 1H), 6.94 (d, 1H), 5.33 (s, 2H).

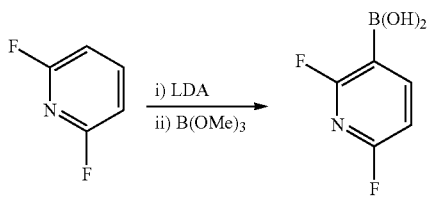 [SMILES: Fc1cccc(F)n1 ; OB(O)c1ccc(F)nc1F]

(2) Synthesis of 2',6'-difluoro-4-methoxy-2,3'-bipyridine[dfpymopy]

Under a nitrogen atmosphere, 0.75 g (4.00 mmol) of 2-bromo-4-methoxy-pyridine, 1.02 g (6.40 mmol) of 2,6-difluoro-pyridyl-3-boronic acid, 0.0374 g (0.032 mmol) of Pd(PPh$_3$)$_4$ were dissolved in 25 mL THF, followed by addition of 10 mL of an aqueous solution of 5 wt % K$_2$CO$_3$, heated to reflux, stirred for 18 h. After naturally cooled to room temperature, an appropriate amount of distilled water was added, and the solution was extracted several times with ethyl acetate, the organic phase were combined and dried over anhydrous MgSO$_4$. After filtration, solvent was removed from the filtrate under reduced pressure to give the crude product. The crude product was purified to silica gel column chromatography using a mixture of ethyl acetate and n-hexane (v/v=1:5) as eluent to obtain 0.54 g of a colorless solid product in 60.7% yield.

$^1$H NMR (400 MHz, CDCl$_3$, ppm): δ8.91 (d, 1H), 8.63 (d, 1H), 7.75 (d, 1H), 7.43 d, 1H), 6.86 (s, 1H), 3.85 (s, 3H).

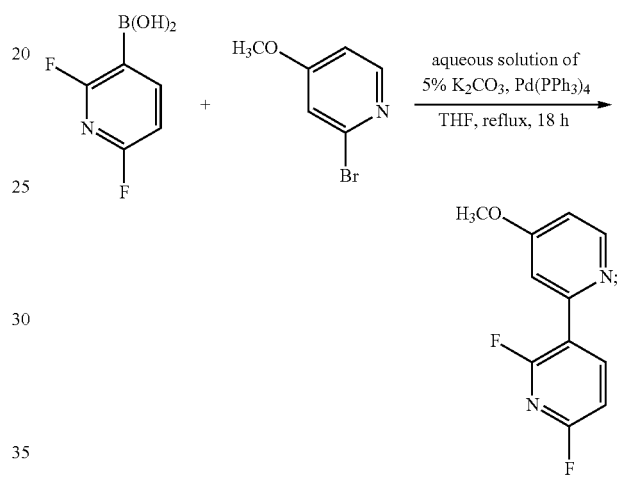

(3) Synthesis of double-bridged compound (dfpymopy)$_2$Ir(μ-Cl)Ir(dfpymopy)$_2$

Under a nitrogen atmosphere, 1.78 g (8 mmol) of 2',6'-difluoro-4-methoxy-2,3'-bipyridine, and 0.71 g (2 mmol) of Iridium trichloride trihydrate were dissolved in 30 mL of 2-ethoxyethanol and heated to reflux, and the reaction solution was stirred for 25 h. After naturally cooled to room temperature, the solution was concentrated under reduced pressure; the crude product was then subjected to silica gel column chromatography using dichloromethane as eluent to obtain 0.94 g of product in 70.1% yield.

$^1$H NMR (400 MHz, CDCl$_3$, ppm): δ 8.82 (d, 4H), 7.66 (d, 4H), 7.35 (d, 4H), 6.74 s, 4H), 3.89 (s, 12H).

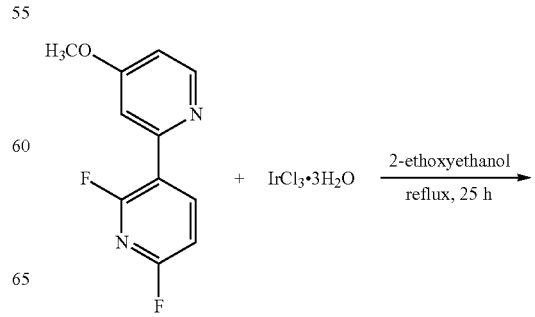

-continued

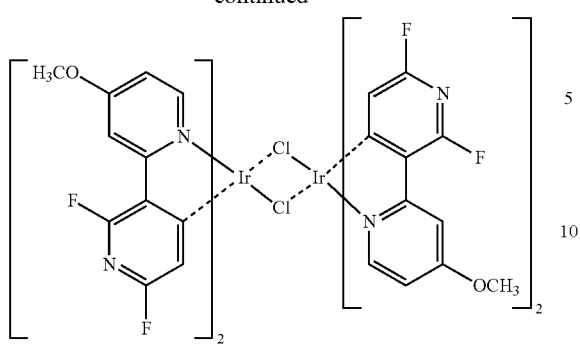

(4) Synthesis of Ligand (dfpymopy)₂Irpic

Under a nitrogen atmosphere, 0.37 g (3 mmol) of 2-picolinic acid and 1.34 g (1 mmol) of double-bridged compound (dfpymopy)₂Ir(μ-Cl)Ir(dfpymopy)₂ were dissolved in 60 mL of 1,2-dichloroethane, under the catalytic effect of 0.54 g (10 mmol) of sodium methoxide and 0.44 g (2 mmol) of silver trifluoroacetate, the reaction solution was stirred and heated to reflux for 24 h. After naturally cooled to room temperature, the reaction solution was concentrated by removing a portion of solvent, an appropriate amount of distilled water was added, and a solid was precipitated out. After filtration, the crude product was collected and the solid was subjected to ultrasonic washing with a sequential use of n-hexane and diethyl ether, which was then subjected to silica gel column chromatography using a mixture of n-hexane: and dichloromethane (v/v=1:3) as eluant to obtain 1.33 g of pure product (dfpymopy)₂Irpym in 87.9% yield.

$^1$H NMR (400 MHz, CDCl₃, ppm): δ 9.03 (d, 1H), 8.51 (d, 1H), 8.49 (d, 1H), 8.32 (d, 1H), 7.92 (t, 1H), 7.78 (t, 1H), 7.55 (m, 1H), 7.52 (m, 1H), 7.20 (d, 1H), 7.18 (d, 1), 6.85 (d, 1H), 6.79 (d, 1H), 3.90 (s, 6H).

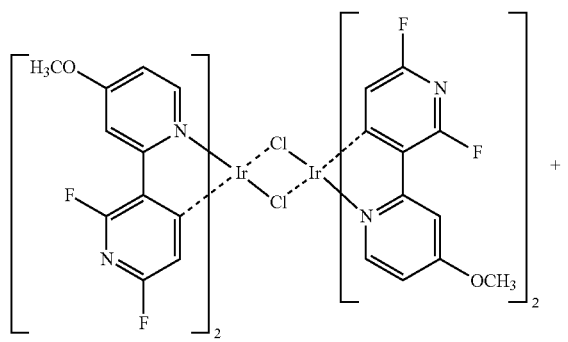

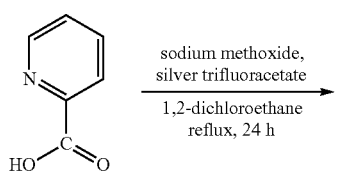

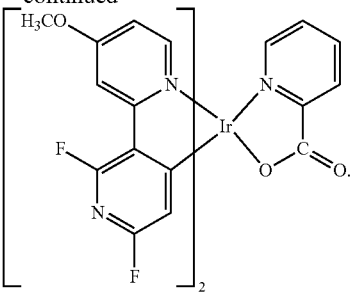

FIG. 1 is the emission spectrum of an organic electroluminescent compound containing Iridium (dfpymopy)₂Irpic in Example 1; wherein, the measurement condition was: at 298K, in a CH₂Cl₂ solution of molar concentration of ~10⁻⁵M; when $\lambda_{max}^{PL}$=449 nm, a shoulder peak was found at 471 nm.

Example 2

The organic electroluminescent compound containing Iridium of the present embodiment, namely Iridium(III)bis(2',6'-difluoro-4-ethoxy-2,3'-bipyridinato-N,C²')(2-picolinato), wherein R is ethyl:

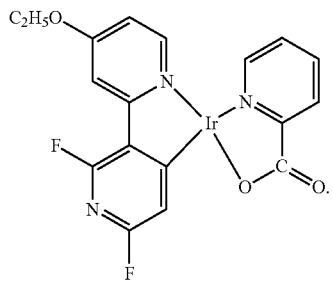

The method of preparing Iridium(III)bis(2',6'-difluoro-4-ethoxy-2,3'-bipyridinato-N,C²')(2-picolinato):

(1) Synthesis of 2,6-difluoro-pyridyl-3-boronic acid is identical to step (1) of Example 1

(2) Synthesis of 2',6'-difluoro-4-ethoxy-2,3'-bipyridine

Under an argon atmosphere, 0.81 g (4.00 mmol) of 2-bromo-4-ethoxy-pyridine, 1.02 g (6.40 mmol) of 2,6-difluoro-pyridyl-3-boronic acid, 0.0374 g (0.032 mmol) of Pd(PPh₃)₄ were dissolved in 30 mL of dioxane, followed by addition of 10 mL of an aqueous solution of 5 wt % K₂CO₃, heated to reflux, stirred for 18 h. After naturally cooled to room temperature, an appropriate amount of distilled water was added, and the solution was extracted several times with ethyl acetate, the organic phase were combined and dried over anhydrous MgSO₄. After filtration, solvent was removed from the filtrate under reduced pressure to give the crude product. The crude product was purified to silica gel column chromatography using a mixture of ethyl acetate and n-hexane (v/v=1:4) as eluent to obtain 0.56 g of a colorless solid product in 59.6% yield.

$^1$H NMR (400 MHz, CDCl₃, ppm): δ 8.92 (d, 1H), 8.65 (d, 1H), 7.75 (d, 1H), 7.43 d, 1H), 6.92 (s, 1H), 4.12 (m, 2H), 1.90 (m, 3H).

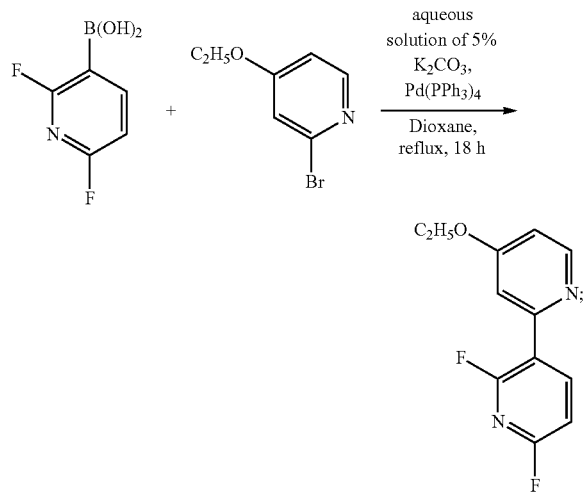

(3) Synthesis of Double-Bridged Compound

Under an argon atmosphere, 1.89 g (8 mmol) of 2',6'-difluoro-4-ethoxy-2,3'-bipyridine, and 0.71 g (2 mmol) of Iridium trichloride trihydrate were dissolved in 30 mL of 2-ethoxyethanol and heated to reflux, and the reaction solution was stirred for 24 h. After naturally cooled to room temperature, the solution was concentrated to remove a portion of solvent; the crude product was then subjected to silica gel column chromatography using dichloromethane as eluent to obtain 0.99 g of product in 70.9% yield.

$^1$H NMR (400 MHz, CDCl$_3$, ppm): δ 8.83 (d, 4H), 7.66 (d, 4H), 7.35 (d, 4H), 6.74 (s, 4H), 4.11 (m, 8H), 1.88 (m, 12H).

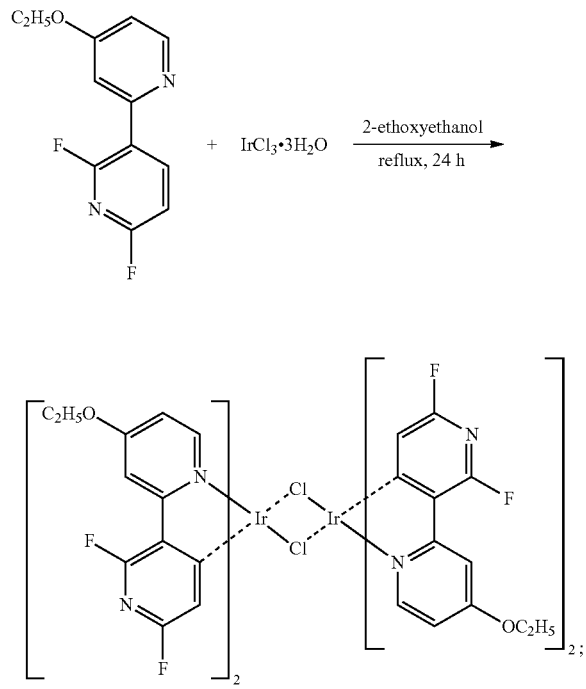

(4) Synthesis of Ligand

Under an argon atmosphere, 0.37 g (3 mmol) of 2-picolinic acid and 1.40 g (1 mmol) of double-bridged compound were dissolved in 60 mL of 1,2-dichloroethane, under the catalytic effect of 0.54 g (10 mmol) of sodium methoxide and 0.44 g (2 mmol) of silver trifluoroacetate, the reaction solution was stirred and heated to reflux for 24 h. After naturally cooled to room temperature, the reaction solution was concentrated by removing a portion of solvent, an appropriate amount of distilled water was added, and a solid was precipitated out. After filtration, the crude product was collected and the solid was subjected to ultrasonic washing with a sequential use of n-hexane and diethyl ether, which was then subjected to silica gel column chromatography using a mixture of n-hexane: and dichloromethane (v/v=1:3) as eluent to obtain 1.26 g of pure product in 80.3% yield.

$^1$H NMR (400 MHz, CDCl$_3$, ppm): δ 9.01 (d, 1H), 8.53 (d, 1H), 8.50 (d, 1H), 8.31 (d, 1H), 7.93 (t, 1H), 7.77 (t, 1H), 7.54 (m, 1H), 7.52 (m, 1H), 7.19 (d 1H), 7.17 (d, 1H), 6.82 (d, 1H), 6.78 (d, 1H), 4.13 (m, 4H), 1.89 (m, 6H).

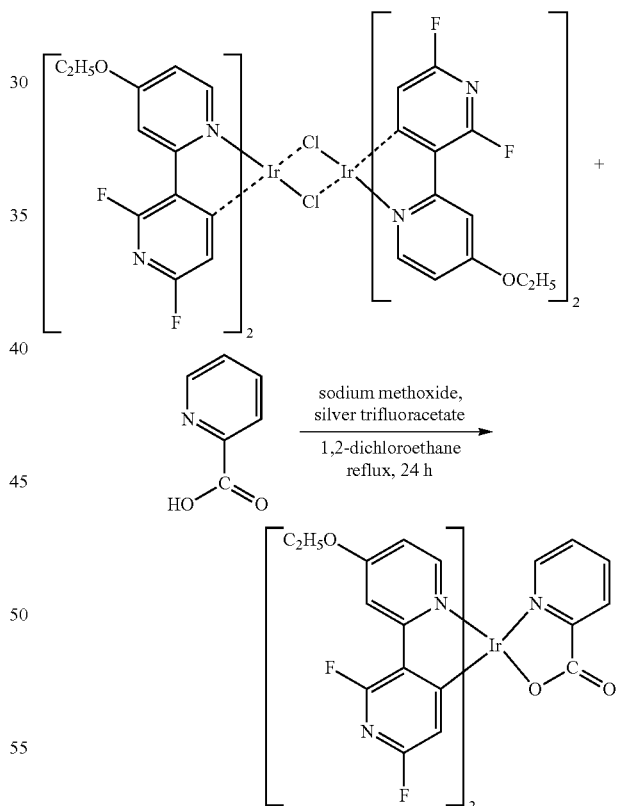

Example 3

The organic electroluminescent compound containing Iridium of the present embodiment, namely Iridium(III)bis(2',6'-difluoro-4-propoxy-2,3'-bipyridinato-N,C$^{2'}$)(2-picolinato), wherein R is propyl:

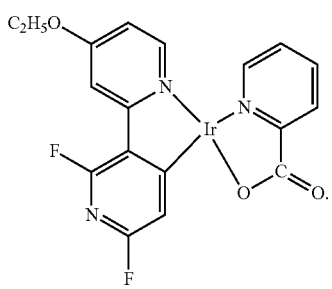

The method of preparing Iridium(III)bis(2',6'-difluoro-4-propoxy-2,3'-bipyridinato-N,C²')(2-picolinato):

(1) Synthesis of 2,6-difluoro-pyridyl-3-boronic acid is identical to step (1) of Example 1

(2) Synthesis of 2',6'-difluoro-4-propoxy-2,3'-bipyridine

Under a nitrogen atmosphere, 0.86 g (4.00 mmol) of 2-bromo-4-propoxy-pyridine, 1.02 g (6.40 mmol) of 2,6-difluoro-pyridyl-3-boronic acid, 0.0374 g (0.032 mmol) of Pd(PPh$_3$)$_4$ were dissolved in 25 mL of dimethyl sulfoxide, followed by addition of 10 mL of an aqueous solution of 5 wt % K$_2$CO$_3$, heated to reflux, stirred for 18 h. After naturally cooled to room temperature, an appropriate amount of distilled water was added, and the solution was extracted several times with ethyl acetate, the organic phase were combined and dried over anhydrous MgSO$_4$. After filtration, solvent was removed from the filtrate under reduced pressure to give the crude product. The crude product was purified to silica gel column chromatography using a mixture of ethyl acetate and n-hexane (v/v=1:4) as eluent to obtain 0.57 g of a colorless solid product in 57.0% yield.

$^1$H NMR (400 MHz, CDCl$_3$, ppm): δ 8.91 (d, 1H), 8.66 (d, 1H), 7.76 (d, 1H), 7.44 d, 1H), 6.91 (s, 1H), 4.08 (m, 2H), 1.76 (m, 2H), 0.98 (m, 3H).

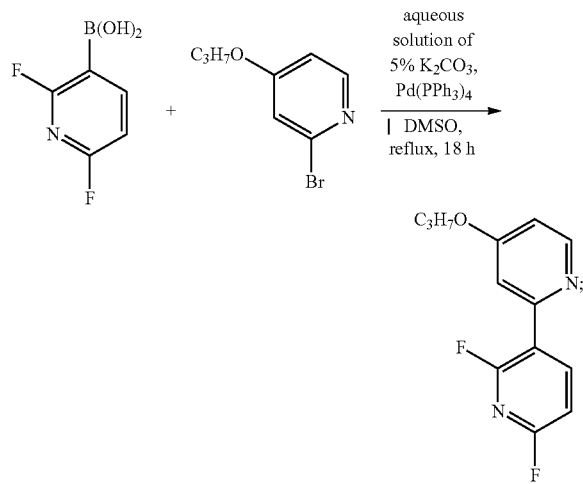

(3) Synthesis of Double-Bridged Compound

Under a nitrogen atmosphere, 2.00 g (8 mmol) of 2'6'-difluoro-4-propoxy-2,3'-bipyridine, and 0.71 g (2 mmol) of Iridium trichloride trihydrate were dissolved in 30 mL of 2-ethoxyethanol and heated to reflux, and the reaction solution was stirred for 24 h. After naturally cooled to room temperature, the solution was concentrated under reduced pressure: the crude product was then subjected to silica gel column chromatography using dichloromethane as eluent to obtain 0.99 g of product in 68.2% yield.

$^1$H NMR (400 MHz, CDCl$_3$, ppm): δ 8.80 (d, 4H), 7.64 (d, 4H), 7.34 (d, 4H), 6.71 (s, 4H), 4.10 (m, 8H), 1.87 (m, 8H), 0.98 (m, 12H).

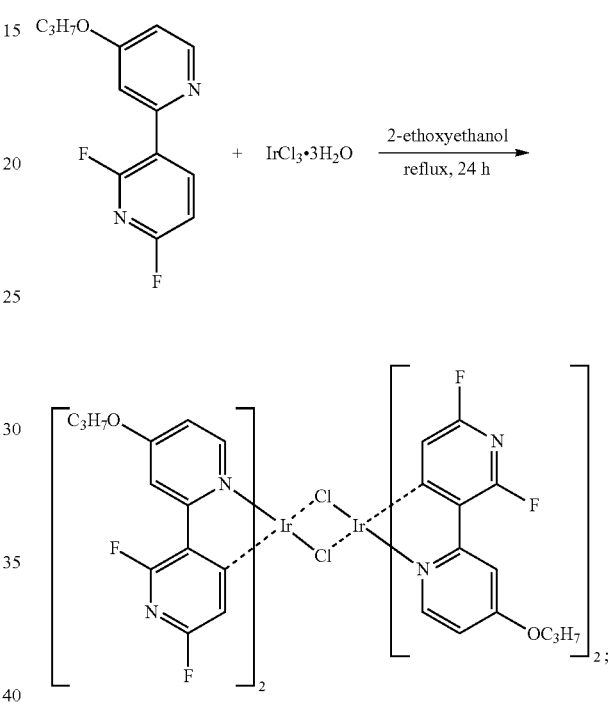

(4) Synthesis of Ligand

Under a nitrogen atmosphere, 0.37 g (3 mmol) of 2-picolinic acid and 1.45 g (1 mmol) of double-bridged compound were dissolved in 60 mL of 1,2-dichloroethane, under the catalytic effect of 0.54 g (10 mmol) of sodium methoxide and 0.44 g (2 mmol) of silver trifluoroacetate, the reaction solution was stirred and heated to reflux for 24 h. After naturally cooled to room temperature, the reaction solution was concentrated by removing a portion of solvent, an appropriate amount of distilled water was added, and a solid was precipitated out. After filtration, the crude product was collected and the solid was subjected to ultrasonic washing with a sequential use of n-hexane and diethyl ether, which was then subjected to silica gel column chromatography using a mixture of n-hexane: and dichloromethane (v/v=1:3) as eluant to obtain 1.34 g of pure product in 82.4% yield.

$^1$H NMR (400 MHz, CDCl$_3$, ppm): δ 9.02 (d, 1H), 8.52 (d, 1H), 8.49 (d, 1H), 8.32 (d, 1H), 7.94 (t, 1H), 7.78 (t, 1H), 7.53 (m, 1H), 7.51 (m, 1H), 7.18 (d, 1H), 7.16 (d, 1H), 6.81 (d, 1H), 6.78 (d, 1H), 4.13 (m, 4H), 1.88 (m, 4H), 0.96 (m, 6H).

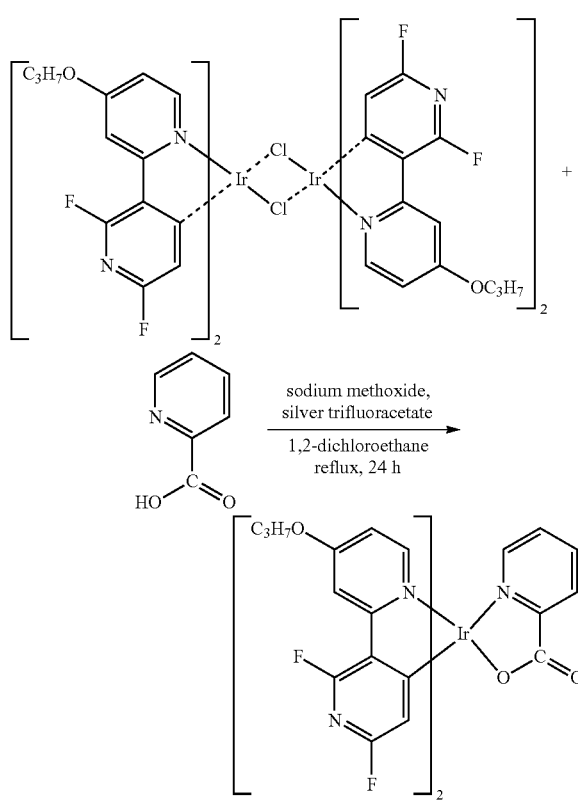

Example 4

The organic electroluminescent compound containing Iridium of the present embodiment, namely Iridium(III)bis(2',6'-difluoro-4-butoxy-2,3'-bipyridinato-N,$C^{2'}$)(2-picolinato), wherein R is butyl:

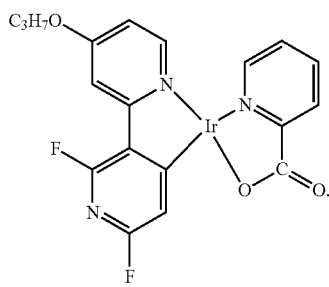

The method of preparing Iridium(III)bis(2',6'-difluoro-4-butoxy-2,3'-bipyridinato-N,$C^{2'}$)(2-picolinato):

(1) Synthesis of 2,6-difluoro-pyridyl-3-boronic acid is identical to step (1) of Example 1

(2) Synthesis of 2',6'-difluoro-4-butoxy-2,3'-bipyridine

Under a nitrogen atmosphere, 0.92 g (4.00 mmol) of 2-bromo-4-butoxypyridine, 1.02 g (6.40 mmol) of 2,6-difluoro-pyridyl-3-boronic acid, 0.0374 g (0.032 mmol) of Pd(PPh$_3$)$_4$ were dissolved in 25 mL of toluene, followed by addition of 10 mL of an aqueous solution of 5 wt % K$_2$CO$_3$; heated to reflux, stirred for 18 h. After naturally cooled to room temperature, an appropriate amount of distilled water was added, and the solution was extracted several times with ethyl acetate, the organic phase were combined and dried over anhydrous MgSO$_4$. Solvent was removed from the filtrate under reduced pressure to give the crude product. The crude product was purified to silica gel column chromatography using a mixture of ethyl acetate and n-hexane (v/v=1:4) as eluent to obtain 0.59 g of a colorless solid product in 55.7% yield.

$^1$H NMR (400 MHz, CDCl$_3$, ppm): δ 8.93 (d, 1H), 8.67 (d, 1H), 7.75 (d, 1H), 7.45 (d, 1H), 6.95 (s, 1H), 4.07 (m, 2H), 1.75 (m, 2H), 1.54 (m, 2H), 0.89 (m, 3H).

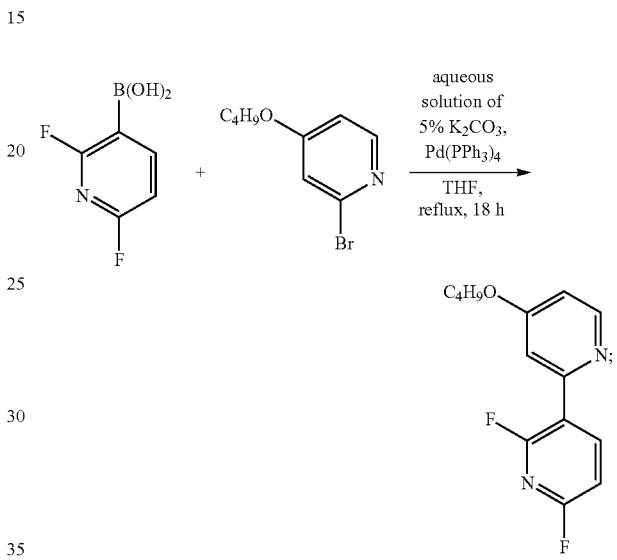

(3) Synthesis of Double-Bridged Compound

Under a nitrogen atmosphere, 2.11 g (8 mmol) of 2',6'-difluoro-4-butoxy-2,3'-bipyridine, and 0.71 g (2 mmol) of Iridium trichloride trihydrate were dissolved in 30 mL of 2-ethoxyethanol and heated to reflux, and the reaction solution was stirred for 24 h. After naturally cooled to room temperature, the solution was concentrated under reduced pressure; the crude product was then subjected to silica gel column chromatography using dichloromethane as eluent to obtain 1.00 g of product in 66.3% yield.

$^1$H NMR (400 MHz, CDCl$_3$, ppm): δ 8.82 (d, 4H), 7.66 (d, 4H), 7.35 (d, 4H), 6.73 (s, 4H), 4.08 (m, 8H), 1.77 ml 8H), 1.53 (m, 8H), 0.90 (m, 12H).

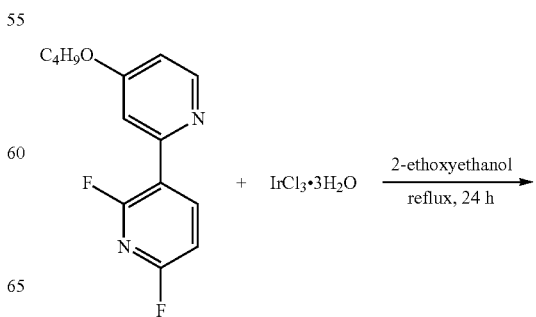

-continued

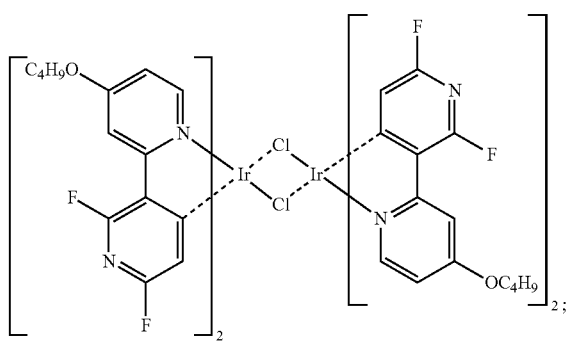

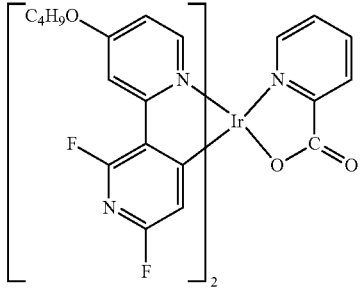

The following Example 5 shows an embodiment of the use of an organic electroluminescent compound containing Iridium in the light emitting layer of an electroluminescent device.

(4) Synthesis of Ligand

Under a nitrogen atmosphere, 0.37 g (3 mmol) of 2-picolinic acid and 1.45 g (1 mmol) of double-bridged compound were dissolved in 60 mL of 1,2-dichloroethane, under the catalytic effect of 0.54 g (10 mmol) of sodium methoxide and 0.44 g (2 mmol) of silver trifluoroacetate, the reaction solution was stirred and heated to reflux for 24 h. After naturally cooled to room temperature, the reaction solution was concentrated by removing a portion of solvent, an appropriate amount of distilled water was added, and a solid was precipitated out. After filtration, the crude product was collected and the solid was subjected to ultrasonic washing with a sequential use of n-hexane and diethyl ether, which was then subjected to silica gel column chromatography using a mixture of n-hexane: and dichloromethane (v/v=1:3) as eluant to obtain 1.30 g of pure product in 77.3% yield.

$^1$H NMR (400 MHz, CDCl$_3$, ppm): δ 9.00 (d, 1H), 8.50 (d, 1H), 8.47 (d, 1H), 8.30 (d, 1H), 7.92 (t, 1H), 7.79 (t, 1H), 7.54 (m, 1H), 7.52 (m, 1H), 7.17 (d, 1H), 7.14 (d, 1H), 6.82 (d, 1H), 6.79 (d, 1H), 4.06 (m, 4H), 1.75 (m, 4H), 1.54 (m, 4H), 0.89 (m, 6H).

Example 5

Figure 2:
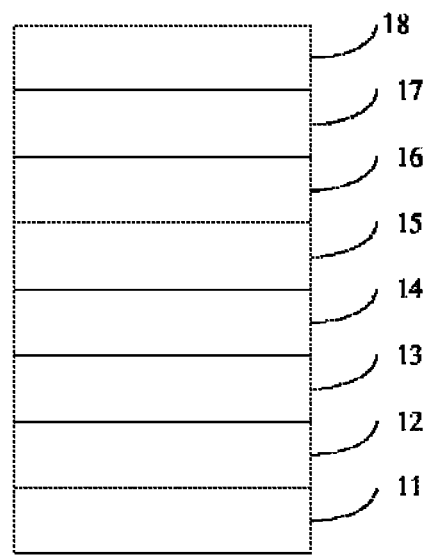
FIG. 2 shows schematically the structure of an electroluminescent device of Example 5.

In this embodiment, Iridium(III)bis(2',6'-difluoro-4-methoxy-2,3'-bipyridinato-N,C$^{2'}$)(picolinato) (hereinafter referred (dfpymopy)$_2$Irpic) obtained in Example 1 was used in the light emitting layer as guest material of doping in the preparation of an organic electroluminescent device. As shown in FIG. 2, the organic electroluminescent device is laminated in structured in the following order: glass 11/ITO layer 12/PEDOT: PSS layer 13/PVK: (dfpymopy)$_2$Irpic layer 14/BCP layer 15/Alq$_3$ layer 16/LiF layer 17/Al layer 18: wherein, PVK is polyvinyl carbazole women; BCP is 2,9-dimethyl-4,7-diphenyl-1,10-phenanthroline; PEDOT is 3,4-ethylenedioxy thiophene; PSS is a polystyrene-sulfonic acid composite material.

The method of preparing said organic electroluminescent device is as follows:

1. On a glass substrate was deposited a layer of indium tin oxide (ITO) having a sheet resistance of 10~20/Ω/□ as a transparent anode;

2. By spin coating, a PEDOT:PSS layer for modification was provided on the ITO layer as a hole transport layer;

3. A light emitting layer was then spin-coated on the surface of the PEDOT:PSS layer, the host material of said light emitting layer is PVK, and the doping material is Iridium(III) bis(2',6'-difluoro-4-methoxy-2,3'-bipyridinato-N,C$^{2'}$)(picolinato) (hereinafter referred (dfpymopy)$_2$Irpic) obtained in Example 1, the doping ratio of PVK:(dfpymopy)$_2$Irpic is 7 wt %;

4. By vacuum deposition, a BCP layer and a LiF layer were deposited successively on the light emitting layer as a hole blocking layer and an electron injection buffer layer, respectively;

5. Finally, a metallic Al layer was deposited on the buffer layer as the cathode of said organic electroluminescent device by vacuum deposition.

Due to the presence of an organic electroluminescent compound containing Iridium having a relatively high color purity and fluorescence quantum efficiency in said organic electroluminescent device, said organic electroluminescent device exhibits relatively high energy conversion efficiency and luminous efficiency, which allows its use in the field of blue or white luminescence.

Although the present invention has been described and illustrated in detail, it is clearly understood that the same is by way of illustrating the preferred embodiment of the present invention and is not to be taken by way of limitation. The present invention should be in the scope of the appended claims prevail.

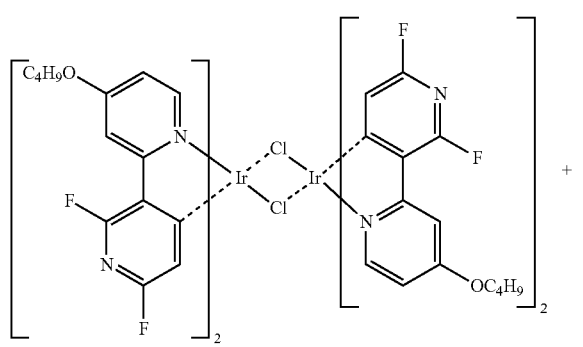

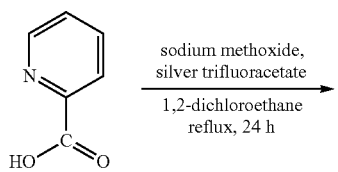

What is claimed is:

1. A method of preparing an organic electroluminescent compound containing Iridium, wherein said method comprises the following steps:

S1: under an oxygen-free atmosphere, compound A of structural formula

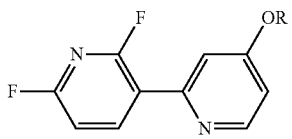

and Iridium trichloride trihydrate in a molar ratio of 3:1 to 5:1 are added to the first organic solvent, and dissolved to react in the formation of double-bridged compound B of structural formula

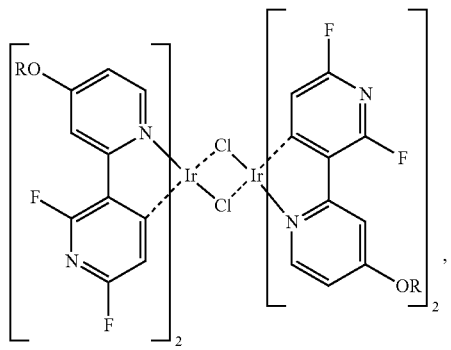

wherein, R is $C_1$~$C_4$ alkyl;

S2: under an oxygen-free atmosphere, said double-bridged compound B and 2-pyridinecarboxylic acid in a molar ratio of 1:2.5 to 1:3.5 are added to the second organic solvent to undergo ligand exchange in the formation of said organic electroluminescent compound containing Iridium of structural formula

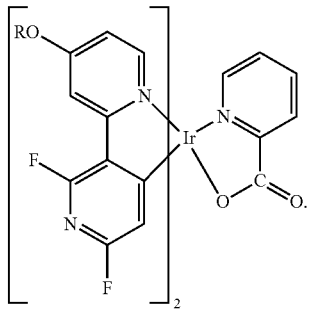

2. A method of preparing an organic electroluminescent compound containing Iridium according to claim 1, wherein in step S1, said compound A is prepared according to the following steps:

S11: under an oxygen-free and anhydrous atmosphere, compound D of structural formula

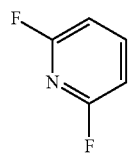

and lithium diisopropylamide in a molar ratio of 1.2:1 are added to a solution of tetrahydrofuran and undergo reaction at −78° C.; trimethyl borate is then added to the reaction mixture to undergo a reaction at room temperature in the formation of compound E of structural formula

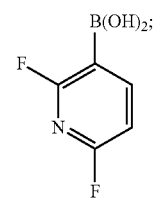 [SMILES: OB(O)c1ccc(F)nc1F]

S12: said compound E and compound F of structural formula

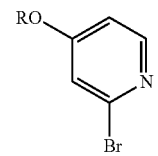

in a molar ratio of 1.5:1~2:1 are added to the third organic solvent containing a catalyst to undergo Suzuki coupling reaction in the formation of said compound A; wherein in said compound F, R is $C_1$~$C_4$ alkyl.

3. A method of preparing an organic electroluminescent compound containing Iridium according to claim 2, wherein said step S11 further comprises the step of purifying said compound E:

quenching the reaction in the reaction mixture with an addition of an aqueous solution of 5 wt % NaOH; adjusting the pH of the reaction mixture to neutral using an aqueous solution of 3N HCl;

extracting the mixture several times with ethyl acetate and combining the organic phases; finally concentrating the organic phase to give the purified compound E.

4. A method of preparing an organic electroluminescent compound containing Iridium according to claim 2, wherein said step S12 further comprises the step of purifying said compound A:

adding distilled water to the reaction mixture containing said compound A; then undergoing extraction, combining the organic phases; drying the organic phase over anhydrous $MgSO_4$, followed by filtration and concentration of the filtrate; finally subjecting the filtrate residue to silica gel column chromatography using a mixture of ethyl acetate and n-hexane as eluent to obtain said purified compound A.

5. A method of preparing an organic electroluminescent compound containing Iridium according to claim 2, wherein in said step S12, said catalyst is a mixture of $K_2CO_3$ solution and $Pd(PPh_3)_4$, the molar amount of $K_2CO_3$ is 10-fold over the molar amount of compound F, the molar amount of Pd(PPh$_3$)$_4$ is 0.5% of the molar amount of compound F.

6. A method of preparing an organic electroluminescent compound containing Iridium according to claim 2, wherein in said step S12, said third organic solvent is tetrahydrofuran, dioxane, toluene or dimethyl sulfoxide.

7. A method of preparing an organic electroluminescent compound containing Iridium according to claim 1, wherein in said step S1, said first organic solvent is 2-ethoxyethanol.

8. A method of preparing an organic electroluminescent compound containing Iridium according to claim 1, wherein in said step S2, said second organic solvent is 1,2-dichloroethane, glycerol, 2-ethoxyethanol or tetrahydrofuran.

* * * * *